United States Patent [19]

Wang et al.

[11] Patent Number: 5,195,969

[45] Date of Patent: Mar. 23, 1993

[54] CO-EXTRUDED MEDICAL BALLOONS AND CATHETER USING SUCH BALLOONS

[75] Inventors: James C. Wang, Norton; George R. Roberts, Arlington; Brian A. Pederson, Sr., So. Attleboro, all of Mass.

[73] Assignee: Boston Scientific Corporation, Watertown, Mass.

[21] Appl. No.: 691,999

[22] Filed: Apr. 26, 1991

[51] Int. Cl.⁵ .............................................. A61M 29/00
[52] U.S. Cl. ........................................ 604/96; 604/103
[58] Field of Search ........................ 604/96, 97, 98, 99, 604/100, 101, 102, 103; 606/191-194

[56] References Cited

U.S. PATENT DOCUMENTS

| | | |
|---|---|---|
| 2,823,421 | 2/1958 | Scarlett . |
| 2,981,254 | 4/1961 | Vanderbilt . |
| 3,045,677 | 7/1962 | Wallace . |
| 3,141,912 | 7/1964 | Goldman et al. . |
| 3,348,542 | 10/1967 | Jackson . |
| 3,707,146 | 12/1972 | Cook et al. . |
| 3,745,150 | 7/1973 | Corsover . |
| 3,889,685 | 6/1975 | Miller et al. . |
| 4,061,170 | 12/1977 | Nohtomi et al. . |
| 4,144,298 | 3/1979 | Lee . |
| 4,233,022 | 11/1980 | Brady et al. . |
| 4,233,443 | 12/1980 | Levy . |
| 4,256,789 | 3/1981 | Suzuki et al. . |
| 4,409,364 | 10/1983 | Schmukler et al. . |
| 4,411,055 | 10/1983 | Simpson et al. . |
| 4,417,576 | 11/1983 | Baran . |
| 4,439,394 | 3/1984 | Appleyard . |
| 4,444,188 | 4/1984 | Bazell et al. . |
| 4,490,421 | 12/1984 | Levy . |
| 4,531,997 | 7/1985 | Johnston . |
| 4,685,447 | 8/1987 | Iversen et al. . |
| 4,693,243 | 9/1987 | Buras . |
| 4,702,252 | 10/1987 | Brooks et al. . |
| 4,751,924 | 6/1988 | Hammerschmidt et al. . |
| 4,820,349 | 4/1989 | Saab . |
| 4,906,244 | 3/1990 | Pinchuk et al. . |
| 4,913,701 | 4/1990 | Tower . |
| 4,938,676 | 7/1990 | Jackowski et al. . |
| 4,941,877 | 7/1990 | Montano, Jr. . |

FOREIGN PATENT DOCUMENTS

| | | |
|---|---|---|
| 0274411 | 5/1988 | European Pat. Off. . |
| 1477423 | 5/1989 | U.S.S.R. ................................ 604/96 |
| 2209121 | 5/1989 | United Kingdom .................. 604/96 |

OTHER PUBLICATIONS

Biaxial Orientation reprinted from Encyclopedia of Polymer Science and Tech., vol. 2 1965 by Wiley & Sons.

*Primary Examiner*—John D. Yasko

[57] ABSTRACT

A medical balloon and a catheter utilizing the balloon and a mechanism to attach the medical balloon to the catheter tube, and method of making the balloon. The attachement mechanism forms a joint and comprises a plurality of co-extruded and coextensive layers of different polymeric materials, at least one of which is a base structural layer and the other of which is formed of polyethylene and copolymers thereof or of Selar. The base structural layer is thicker then the other layer. The attachment mechanism can be the balloon itself or it can be a sleeve, either of which is heat sealed to the catheter tube. In either case, the diameter of the catheter at the joint is substantially the same as the tube.

16 Claims, 1 Drawing Sheet

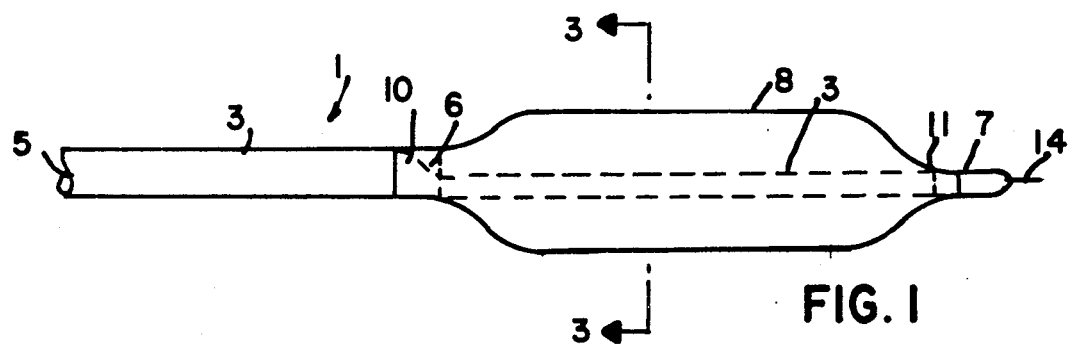
FIG. 1
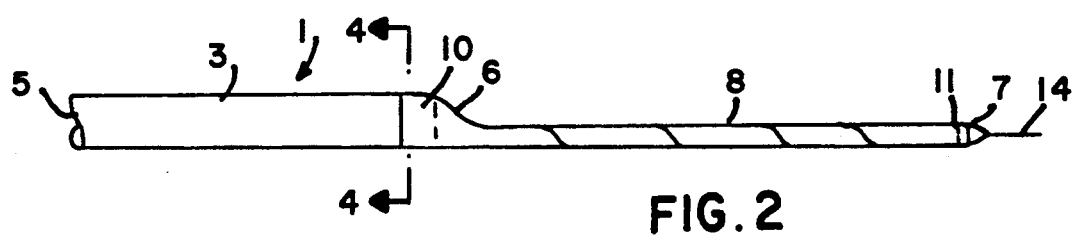
FIG. 2
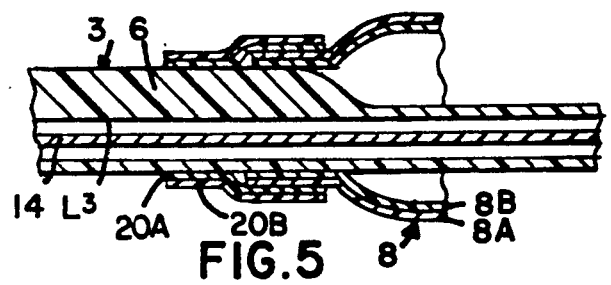
FIG. 5
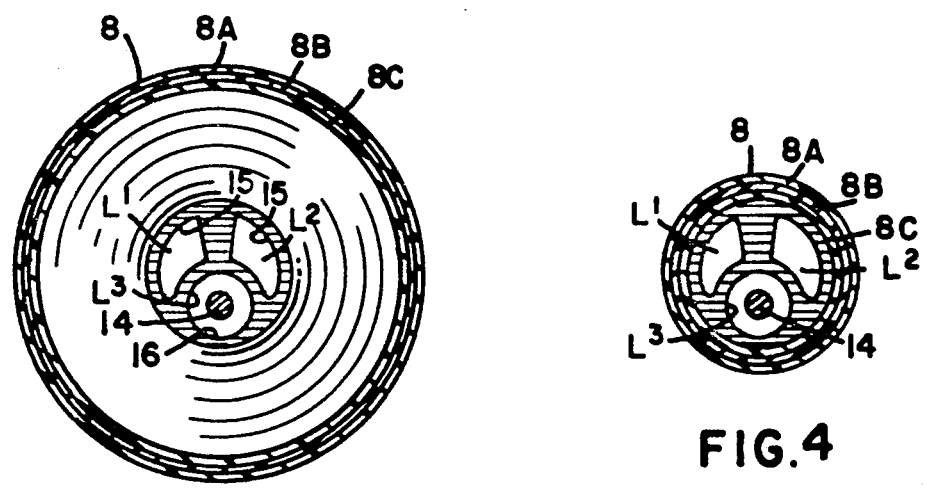
FIG. 3
FIG. 4

CO-EXTRUDED MEDICAL BALLOONS AND CATHETER USING SUCH BALLOONS

BACKGROUND OF THE INVENTION

The present invention relates to balloons for medical devices and medical devices utilizing such balloons. More particularly, the present invention relates to medical or surgical balloons and catheters using such balloons, particularly those designed for angioplasty, valvuloplasty and urological uses and the like. The balloons of the present invention can be tailored to have expansion properties which are desired for a particular use and can be inflated to a predetermined diameter and still be resistant to the formation of pin holes and leakage.

DESCRIPTION OF THE PRIOR ART

In the past, polyethylene, polyethylene terapthalate and polyamide balloons have been used with medical catheters. Polyethylene balloons are particularly advantageous because they can be heat bonded to a like-material substrate and have a relatively low tip diameter, that is the profile of the tip at the connecting joint between the balloon and the catheter can be fairly small. Also, the polyethylene balloons are soft so that they can pass through blood vessels without trauma. Moreover, polyethylene balloons are resistant to the propagation of pin holes, primarily because the walls are thick. But since they are thick, they are large and pass by tight lesions only with great difficulty.

Balloons of polyethylene terapthalate provide low deflated profiles and can have thin walls because such materials have high tensile strengths and adequate burst strength. On the other hand, polyethylene terapthalate balloons require adhesives to bond them to the catheters and adhesive bonding frequently is not dependable and it thickens the catheter at the point of the bond. Moreover, polyethylene terapthalate can have poor pin hole resistance largely due to the very thin walls.

SUMMARY OF THE INVENTION

According to the present invention, it has been discovered that the drawbacks of the polyethylene and the polyethylene terapthalate balloons of the prior art can be remedied through the use of laminated balloon constructions which comprise a tubular body formed of a plurality of co-extruded and co-extensive layers of different polymeric materials.

According to one aspect of the invention, the multi-layered balloon combines the advantages of both materials in a balloon, but does not have the disadvantages of either. The balloon includes a layer of a relatively thick, biaxially oriented ethylenic polymeric material such as polyesters, polycarbonates, polyethylene terapthalate and their copolymers, or polyamides such as Nylon. These materials constitute a base structural layer (or layers) and give the balloon its tensile strength and provide for "wear" resistance. The base structural layer may have a thickness between about 0.2 and 1.0 mil. or higher. A second layer is co-extruded with the base structural layer and is co-extensive therewith. The second layer preferably is a polyolefin such as polyethylene and copolymers thereof and can be heat-bonded to a catheter, that is adhesives need not be used. The heat bondable second layer can be disposed on one and preferably both sides of the base structural layer.

In accordance with another aspect of the present invention, the base structural layer again is a material that does not itself readily thermally bond to a polyethylene catheter tubing. In those cases, sleeves of mutually bondable materials are slipped over the joints between the catheter and the balloon and the sleeves are heated to join the balloon to the sleeve and simultaneously join the sleeve to the catheter whereby to act as a fluid-tight seal between the catheter and the balloon.

With regard to multilayered balloons, the second layer (or layers) which is disposed on the base structural layer and co-extruded therewith can also serve as a barrier between the base structural layer and the environment. For example, when a polyamide such as Nylon is used as the base structural layer, a thin layer of maleic anhydride-modified ethylenic polymers such as Plexar can also be co-extruded with it. When layers are disposed on both sides of the base structural layer they keep moisture from effecting the Nylon's properties. Additional layers sometimes may also be co-extruded to bind and tie dissimilar layers together in the co-extrusion operation. When Nylon is used, for example, no tying layers are necessary between it and the heat bondable layer. In other cases, however, as when polyester or polycarbonate polymers are used as the base structural layer, adhesion enhancement may be necessary. Such adhesive enhancement may take the form of ultraviolet light irradiation of the product or the incorporation of a co-extruded tying adhesive layer.

With regard to the use of a multilayered sleeve to join the balloon to the catheter, any conventional medical balloon material can be used that does not bond to the catheter without adhesives. The multiayered sleeve can be formed of a base layer of the same material as the balloon with a polyethylene layer disposed on at least the inner side of the sleeve. The polyethylene will adhere to both the catheter and the balloon and form a joint with heat treatment alone.

According to the present invention, the balloons have advantages of both the polyethylene and the materials of the base structural layer. When polyethylene terapthalate is the base, very thin walls can be used with high burst strength. For example, when a typical 3.0 mm. diameter maleic anhydride modified ethylenic polymer layer is co-extruded with a Nylon base structural layer, the resulting balloon can have a wall thickness of 0.5 mil. and a low deflated profile which is comparable with polyethylene terapthalate balloons and is much lower than polyethylene balloons. When using Nylon, the material that is used is biaxially orientable and has higher tensile strength than polyethylene material, thereby resulting in a much thinner wall for comparative burst strength.

It has been found that pin hole resistance of the construction of the present invention is comparable to polyethylene and substantially superior to polyethylene terapthalate. A balloon co-extruded with Selar has superior abrasion resistance and pin hole resistance than polyethylene terapthalate balloons. Polyamide material is superior to polyethylene terapthalate and polyethylene materials in pin hole resistance. The balloon itself is soft for non-traumatic passage through blood vessels and is comparable to polyethylene because polyamide is not as stiff as polyethylene terapthalate.

In a specific embodiment of a multilayered extruded balloon, it has been found that the use of the above mentioned Selar PT resin, a trademarked compound (preferably available as Selar PT 4368 from E. I. Dupont de Nemaurs Co. of Wilmington, Del.) as a layer disposed on the base structural layer (or blended with polyethylene terapthalate) will make the balloon more resistant to abrasion and provide it with a softer feel. Selar coextrusion in multi-layered balloons diminishes pin hole formation and will minimize failure when working with calcified lesions. Moreover, the Selar may be used as the inner layer of the balloon for use with procedures which include internal electrodes or radiopaque markers which could puncture it.

BRIEF DESCRIPTION OF THE DRAWINGS

FIG. 1 is a side elevational view of a catheter with a multi-layered balloon. The balloon is shown in the distended condition;

FIG. 2 is a view of the same catheter in the folded condition;

FIG. 3 is a cross-sectional view of the balloon of the present invention taken along the line 3—3 of FIG. 1 showing the polymeric layers in the balloon;

FIG. 4 is a cross-sectional view taken along the line 4—4 of FIG. 2 showing the balloon in its folded condition; and FIG. 5 is a cross sectional view of a distended balloon disposed at the end of a catheter and joined to the catheter by a sleeve.

DESCRIPTION OF THE PREFERRED EMBODIMENTS

An illustrative catheter 1 is shown in FIGS. 1 and 2. Catheter 1 includes a catheter tube 3 having a proximal end 5 a distal end 6 and a tip 7. A distended coextruded medical balloon 8 of the present invention is shown in FIG. 1 secured to the outside of the distal end 6 and the tip 7, the co-extrusion being critical to the present invention. The interior of the balloon 8 is in communication with at least one lumen (not shown in this Figure) of the catheter tube 3. To form the tip 7 (and the portion of the catheter between the distal end 6 and the tip 7 to support the balloon 8) a portion of the catheter tube 3 is cut away so that only the lumen that houses an internal guide wire 14 remains (as shown in dotted lines within the balloon 8).

Extending through the interior of the tube 3 are a plurality of lumens (shown in FIGS. 3 and 4) which can serve a variety of functions, for example, housing the guide wire 14, inserting materials into the blood stream or inflating or deflating the balloon. Except for the balloon 8, all of the various components perform functions which are generally appreciated and known in the art.

To use, the catheter 1 (as shown in FIG. 2) is inserted into the cardiovascular system until the coextruded balloon 8 is located at the site of an occlusion. At this stage, the balloon 8 is typically folded and collapsed and has an external diameter less than the inflated diameter, as can be seen by a comparison of FIGS. 1 and 2. Once the balloon 8 is maneuvered to the location of the occlusion, a pressurizing fluid is inserted at the proximal end 5 of the catheter tube 3 for inflation of the balloon 8. The fluid unfolds the balloon 8 until it presents a relatively smooth expanded profile for imparting forces that are radially outwardly directed at the desired site within the body in order to achieve the desired result of lesion dilation, restriction reduction or similar treatment.

Inserting the catheter 1 in an artery requires that the tube 3 be of a semi-flexible material. Tube 3 preferably is composed of a polyolefin copolymer, for example a conventional high density polyethylene. The diameter of the tubing is between about 12 and 16 French and may be coated on the inside and outside surfaces with, for example, a silicone based material to promote slippage in an aqueous environment.

As seen in FIGS. 3 and 4, the co-extruded balloon 8 results in a laminated construction. The laminates of the construction include a main structural layer 8B which is generally between about 0.2 and 2.5 mil. or thicker, and formed of one or more biaxially oriented polymers such as polyamides, polyesters, polycarbonates and their copolymers. Co-extruded with and bonded to the structural layer 8B is an inner layer 8C of heat bondable polyolefin such as Plexar. Plexar is an anhydid-modified polyethylene and a trademarked product sold by Quantum Chemical Corporation of Cincinnati, Ohio. The heat bondable layer 8C is attached directly to the distal end 6 of catheter tube 3 and is secured to the balloon 8 by a heat seal joint 11. A similar joint 11 is formed between the balloon 8 and the catheter tip 7.

The heat bondable layer 8C is co-extruded with the structural layer 8B and has a thickness of between about 0.5 and 1.0 mil. Preferably, two heat bondable layers are co-extruded with the structural layer 8B. The inner layer 8B serves as a mechanism to provide a heat seal joint 10 between the distal end 6 of the catheter tube 3 and the structural layer 8B of the balloon 8. When two layers are co-extruded with the structural layer 8B, the inner layer 8C forms the heat bondable layer and the outer layer 8A forms a protective sheath for the main structural layer 8B. When polyamides such as Nylon are used as the structural layer 8B, Plexar can be used as the heat bonding layer 8C. The outer layer 8A can be formed of the same material and provide for softness for non-traumatic passing through vessels and good pin hole resistance.

An alternative to the construction shown in FIG. 1, another construction is to dispose a balloon formed of a base structural layer 8B of polyethylene terapthalate and an outer layer 8A of polyethylene around the distal end 6 of the catheter tube 3 and then place a sleeve 20 formed of heat bonding layer 20C of high density polyethylene on a base layer 20B Nylon over the end of the balloon 8 whereby the polyethylene of the balloon seals to the polyethylene of the sleeve and the Nylon seals to the catheter 3. In cases where additional strength is needed, an innermost layer can be formed of high density polyethylene and an outermost layer is formed of Nylon with Plexar sandwiched therebetween.

It has been found that where strength, abrasion resistance and/or "feel" are important in medical balloons, that a co-extrusion which includes Selar resin can be used to provide for these characteristics. The Selar can be used by itself as the inner and/or outer layer or it can be blended with polyethylene terapthalate. Tests of a 1.6 mil. thick balloon with a Selar outer layer (a 50/50 blend of Selar and polyethylene terapthalate) were conducted by rubbing a balloon inflated to 6 atm. and rubbing it back and forth over medium grade emery cloth until failure. The balloons with Selar or 50/50 blend layers exceeded 200 cycles while a 1.8 mil. thick polyethylene terapthalate balloon failed in 87 cycles. Selar is a toughened grade of polyethylene terapthalate and it can be co-extruded with the base structural layers herein disclosed according to known techniques.

Referring to FIGS. 3 and 4, the interior of the co-extruded balloon 8 is shown in cross section. In FIG. 3, the balloon is shown in its distended or inflated condition whereas in FIG. 4 the balloon is shown in its deflated or folded condition. The balloon 8 can typically have an outer diameter that can be on the order of roughly three to six and even more times the outer diameter of the catheter tube 3. Pressurized fluids are used to inflate the balloon include and those conventionally used in the art, such as the well known aqueous solutions can be used if they do not pose a problem of leaving residual fluids or chemically reacting with the balloon. Such fluids are introduced into the balloon 8 and removed therefrom through a lumen $L^1$ which is in fluid flow relationship with the interior thereof. Venting of gasses initially trapped in the catheter and the balloon prior to introduction of the inflation fluids is accomplished by expelling them through a second lumen $L^2$ also formed in the interior of the catheter tube 3. Preferably, lumen $L^1$ and $L^2$ are cut off at joint 10 so as to leave only a third lumen $L^3$.

The third lumen $L^3$ houses a guide wire 14 that passes through the balloon 8 and the tip 7. The third lumen $L^3$ is different than the other two lumens, $L^1$ and $L^2$, in that it extends entirely through the balloon 8 from the distal end 6 to the tip 7 so as to sheath the guide wire. In some embodiments, it may be desirable to combine the functions of lumens, $L^1$ and $L^2$, to only have a single lumen for inflating or deflating the balloon Lastly, the lumen defined by $L^3$ provides for a housing for a guide wire 14 which may be removably housed in it. Guide wire 14 passes through the entire length of the catheter 3 and through the balloon 8 (while preferably sheathed in lumen $L^3$ and thence into a axial bore (not shown) in tip 7 to emerge from the end of tip 7 (as shown in FIGS. 2 and 3).

Each of the lumens $L^1$, $L^2$ and $L^3$ is formed by walls 15 and 16 that are extruded as the catheter tube is extruded from an extrusion machine, as is well known in the art. The thickness of the walls 15 and 16 can be between 0.5 and 10 mil. as is well known.

As shown in FIG. 4, the diameter of the folded balloon 8 is substantially the same or less than the diameter of the catheter tube 3 so as to provide for easy passage of the catheter through blood vessels. The extruded tubing 3 has a nominal wall thickness that generally is on the order of six to twelve times the desired wall thickness of the balloon 8.

To form the co-extruded balloons, the materials initially are melted separately in extrusion machines. When melted, the materials are separately forced into an extrusion head and extruded so that they are forced out as a plurality of layers in the form of a single tube which critically forms the balloon of the present invention. A Nylon-Plexar or polyethylene-polyethylene terapthalate balloon may be formed by taking a six inch length of the three layered tubing which is to be manufactured into a balloon and in a holding fixture. The left hand end of the tube is attached to a Touhy Borst adapter. The right hand end of the tube is heat sealed to temporarily prevent pressurized air from escaping. The right hand end is attached to a tension line which is pulled for the force of a least 150 grams (for a 3.0 mm. diameter balloon). The tubing is heated under a pressure of between about 100 and 400 psi to about 210° F. for several seconds. Afterwards, the heated area is cooled and the support frame is spread apart slightly so as to expose a predetermined section of tubing to permit the balloon area to be reheated to a temperature between about 210° and 220° F. to permit the balloon to be expanded to a desired diameter under pressure for about 35 seconds. The pressure is then stopped and the deflectors are slid to the ends of the balloon and the balloon is heated for a third time to about 310° F. to heat set the balloon and biaxially orient the polymeric matrix. This third heating prevents the balloon layers from flaking and prevents the balloon from expanding beyond the size at which it will set during the heat setting period. The heat setting takes about 8 seconds.

For a Nylon-Plexar balloon, the deflectors from the tubes are then removed and another unheated tube is mounted into the fixture. The catheter tube is slid inside the balloon so that it engages the heat bondable polyethylene layer. The balloon is bonded to the polyethylene shaft by heat bonding in a temperature of about 310° F. which is long enough the melt the polyethylene end and the inner layer of the polyethylene together.

It is quite important to recognize that the heat treatment steps as described herein essentially prevent the delamination of the heat bondable layers 8C and 8A from the main structural layer 8B as is required when a laminated construction is used as a catheter. Flaking and delamination is not a problem however, with polyethylene teraphthalate and Selar layers.

While it is apparent that modifications and changes may be made within the spirit and scope of the present invention. It is intended, however, only to be limited by the scope of the appended claims.

We claim:

1. A catheter for medical purposes, said catheter comprising:
    a tubular member having a distal end and at least one lumen disposed therethrough;
    a balloon having at least one open end, said open end being sealed at a joint to said distal end, the interior of said balloon being in communication with said lume.1, said balloon having an elongated tubular body and comprising a plurality of co-extruded layers of different polymeric materials, at least one of said layers being a polyolefin that is sealed by heat to said tubular member.

2. The catheter according to claim 1 wherein the other of said layers is formed of a material comprising polyethylene and copolymers thereof.

3. The catheter according to claim 1 wherein the diameter of the tubular member and the diameter of said joint is substantially the same.

4. The catheter according to claim 1 wherein another of said layers is a base structural layer and has a thickness between about 0.2 and about 2.5 mil. and the other layer has a thickness between about 0.15 and 1.0 mil.

5. The catheter according to claim 1 wherein said balloon has at least three co-extruded layers, one of said layers being a base structural layer, said base structural layer being disposed between the two layers at least one of which is the heat sealed layer.

6. The catheter according to claim 1 wherein said balloon has a base structural layer, said base structural layer being a member selected from the group consisting of polyamides, polycarbonates, polyesters and copolymers thereof.

7. The catheter according to claim 1 wherein the heat sealable layer of said balloon is a member selected from the group consisting of polyethylene and copolymers thereof.

8. The catheter according to claim 1 wherein the tubular member is formed of a polyolefin comprising polyethylene and said polyolefin is a member selected from the group consisting of polyamides, polycarbonates, polyesters and copolymers thereof and said heat sealable layer is a member selected from the group consisting of polyethylene and copolymers thereof.

9. The catheter according to claim 1 wherein said balloon has two open ends, said catheter further comprising a distal tip, said distal tip being heat sealed to said balloon.

10. A catheter for medical purposes, said catheter comprising:
   a tubular member having a distal end and at least one lumen disposed therethrough;
   a balloon having at least one open end, said open end being sealed at a joint to said distal end, the interior of said balloon being in communication with said lumen, said balloon having an elongated tubular body and comprising a plurality of co-extruded layers of different polymeric materials, at least one of said layers being a base structural layer and the other of said layers being formed of a Selar.

11. A catheter for medical purposes, said catheter comprising:
   a tubular member having a distal end and at least one lumen disposed therein;
   an elongated medical balloon having an open end, said open end being fitted over a joint at said distal end of said tubular member, the interior of said balloon being in communication with said lumen, said balloon having an elongated, expandable tubular body and comprising a plurality of co-extruded layers of different polymeric materials, neither of which is heat sealed to said tubular member;
   a sleeve for connecting said medical balloon to said tubular member, said sleeve being disposed over said joint and comprising an elongated tubular body having a predetermined diameter and adhering to both said medical balloon and said catheter, said sleeve comprising a plurality of co-extruded and coextensive layers of different polymeric materials, at least one of said layers being a polymeric layer and another of said layers being selected from the group consisting of polyethylene and copolymers thereof.

12. The catheter according to claim 11 wherein said tubular member is formed of a material comprising polyethylene and copolymers thereof.

13. The catheter according to claim 11 wherein the diameter of the tubular member and the diameter of the joint is substantially the same.

14. The catheter according to claim 11 wherein the balloon has a layer selected from the group consisting of polyamides, polycarbonates, polyesters and copolymers thereof.

15. The catheter according to claim 11 wherein the sleeve has a layer selected from the group consisting of polyamides, polycarbonates, polyesters and copolymers thereof.

16. The catheter according to claim 11 wherein said balloon has two open ends, said catheter further comprising a tip disposed on the other open end, said tip being heat sealed to said balloon.

* * * * *